United States Patent [19]

Rösch et al.

[11] Patent Number: 5,700,758

[45] Date of Patent: Dec. 23, 1997

[54] PYRAZOLINES FOR PROTECTING CROP PLANTS AGAINST HERBICIDES

[75] Inventors: Wolfgang Rösch, Frankfurt am Main; Erich Sohn, Augsburg; Klaus Bauer, Hanau; Hermann Bieringer, Eppstein/Taunus, all of Germany

[73] Assignee: Hoechst Aktiengesellschaft, Frankfurt, Germany

[21] Appl. No.: 468,850

[22] Filed: Jun. 6, 1995

Related U.S. Application Data

[62] Division of Ser. No. 848,998, Apr. 21, 1992, abandoned.

[30] Foreign Application Priority Data

Nov. 30, 1989 [DE] Germany .................. 39 39 503.0

[51] Int. Cl.$^6$ .................... A01N 25/32; A01N 43/56; A01N 43/86; C07D 231/06
[52] U.S. Cl. .................... 504/106; 548/357.5; 548/374.1
[58] Field of Search .................................. 504/106

[56] References Cited

U.S. PATENT DOCUMENTS

| | | | |
|---|---|---|---|
| 4,602,932 | 7/1986 | Handte et al. | 71/92 |
| 4,639,266 | 1/1987 | Heubach et al. | 71/92 |
| 4,891,057 | 1/1990 | Sohn et al. | 71/72 |
| 4,937,395 | 6/1990 | Litterer et al. | 570/142 |
| 4,944,790 | 7/1990 | Moser et al. | 71/92 |
| 5,037,468 | 8/1991 | Sohn et al. | 71/92 |

FOREIGN PATENT DOCUMENTS

| | | |
|---|---|---|
| 11544/88 | 9/1988 | Australia . |
| 0 269 806 | 9/1987 | European Pat. Off. . |
| 3808896 | 9/1989 | Germany . |
| 38 24 141 | 1/1990 | Germany . |
| 3923649 | 1/1991 | Germany . |
| 89/1960 | 10/1989 | South Africa . |
| WO 88/06583 | 9/1988 | WIPO . |

OTHER PUBLICATIONS

Smolik et al., "Decarbonylation of Aromatic Aldehydes on Platinum Metal Catalysts." *Collection Czechoslov. Chem. Commun.*, 37 (1972), 3042–3051.

*Primary Examiner*—S. Mark Clardy
*Attorney, Agent, or Firm*—Curtis Morris & Safford P.C.

[57] ABSTRACT

Compounds of the formula (I)

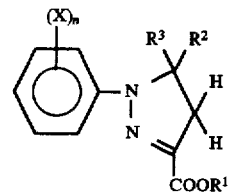

where

X, n, $R^1$, $R^2$ and $R^3$ are as defined in claim 1 are suitable as antidotes against phytotoxic secondary effects of herbicides in crop plants without adversely affecting the action of the herbicides against harmful plants.

31 Claims, No Drawings

PYRAZOLINES FOR PROTECTING CROP PLANTS AGAINST HERBICIDES

This application is a division of application Ser. No. 07/848,998, filed as PCT/EP90/02020 Nov. 26, 1990 published as WO91/07874 Jun. 13, 1991, abandoned.

When herbicides are used, it is possible that undesirable damage occurs on crop plants, and this cannot be tolerated. There is therefore often a demand of avoiding the risk of a potential phytotoxicity, particularly when herbicides are applied after the crop plants have emerged.

Such compounds which have the properties of protecting crop plants against phytotoxic damage due to herbicides without adversely affecting the actual herbicidal action of these agents are antidotes or safeners.

A range of compounds has already been described for this application (cf., for example, EP-A 152,006 and EP-A 0,174,562).

German Patent Application P-3,808,896.7 proposed 1-phenyl- and 1-(pyrid-2-yl)-pyrazole derivatives as safeners.

The use of alkoxypyrazolines as safeners was proposed in German Patent Application P 3,923,649.8 (HOE 89/F 235).

The present invention relates to agents which protect crop plants and which contain 4,5-pyrazoline-3-carboxylic ester derivatives of the formula (I)

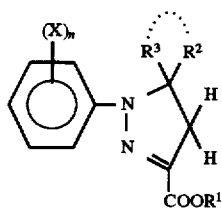

where

X radicals independently of one another are halogen or haloalkyl, n is an integer from 1 to 3, $R^1$ is hydrogen, alkyl, cycloalkyl, trialkylsilyl, trialkylsilylmethyl or alkyloxyalkyl, $R^2$ and $R^3$ independently of one another are hydrogen, alkyl, $C_3$–$C_6$-cycloalkyl, alkenyl, alkynyl, haloalkyl, alkoxyalkyl, hydroxylalkyl, alkoxycarbonyl, alkylcarbonyl, alkylaminocarbonyl, optionally substituted phenyl, halogen or cyano, it being possible for the radicals $R^2$ and $R^3$ to form a ring with the 5-C atom of the pyrazoline ring.

Formula (I) in this context embraces all geometric isomers and stereoisomers which are possible. In formula (I), halogen is fluorine, chlorine, bromine or iodine, alkyl is straight-chain, branched or cyclic alkyl, alkenyl is straight-chain or branched alkenyl, it being possible for the double bond to be in any position in the alkenyl radical, and alkynyl is straight-chain or branched alkynyl, it also being possible for the triple bond in this case to be in any position in the alkynyl radical, haloalkyl is alkyl which is monosubstituted or polysubstituted by halogen, and alkoxyalkyl and hydroxyalkyl are alkyl radicals which are monosubstituted or polysubstituted by alkoxy or hydroxyl. The meanings mentioned in the case of alkyl are also valid for the alkyl radicals contained in combinations such as alkyloxyalkyl, alkyloxycarbonyl and alkylaminocarbonyl.

Agents according to the invention which are of particular interest are those with compounds of the formula (I) where X radicals independently of one another are halogen or $C_1$–$C_4$-haloalkyl, n is an integer from 1 to 3, $R^1$ is $C_1$–$C_6$-alkyl, $C_3$–$C_6$-cycloalkyl, tri($C_1$–$C_4$-alkyl)silyl, tri($C_1$–$C_4$-alkyl)silylmethyl or ($C_1$–$C_6$-alkyloxy)-$C_1$–$C_6$-alkyl, $R^2$ and $R^3$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, mono- or di-($C_1$–$C_4$-alkoxy)-$C_1$–$C_4$-alkyl, $C_1$–$C_6$-hydroxyalkyl, ($C_1$–$C_6$-alkyl)carbonyl, mono- or di-($C_1$–$C_4$-alkyl)aminocarbonyl, cyano, halogen, ($C_1$–$C_{12}$-alkyl)oxycarbonyl, phenyl, or phenyl which is substituted by one or more radicals selected from the group comprising halogen, $C_1$–$C_4$-alkyl, $C_1$–$C_4$-alkoxy or cyano.

Haloalkyl is preferably trifluoromethyl, 2-chloroethyl, 1,1,2,2-tetrafluoroethyl or hexafluoropropyl; halogen is preferably fluorine, chlorine or bromine.

Alkyl is preferably one of the radicals methyl, ethyl, n-propyl, i-propyl, the butyl, pentyl and hexyl isomers, cyclopentyl and cyclohexyl. Alkenyl is preferably one of the radicals vinyl, 1-propen-1-yl, 1-propen-2-yl, and the butenyl, pentenyl and hexenyl isomers. Alkynyl is preferably ethynyl, 1-propynyl or 2-propynyl.

Preferred agents according to the invention are those with compounds of the formula (I) where X radicals independently of one another are fluorine, chlorine, bromine or trifluoromethyl, preferably in each case in the 2- or 4-position, n is 2 or 3, $R^1$ is $C_1$–$C_4$-alkyl or ($C_1$–$C_4$-alkoxy)-$C_1$–$C_4$-alkyl, $R^2$ is hydrogen, $C_1$–$C_4$-alkyl or $C_2$–$C_4$-alkenyl, $R^3$ is $C_1$–$C_4$-alkyl, $C_3$–$C_4$-alkenyl, $C_2$–$C_4$-alkynyl, $C_1$–$C_4$-haloalkyl, mono- or di-($C_1$–$C_4$-alkoxy)-$C_1$–$C_4$-alkyl, $C_1$–$C_4$-hydroxyalkyl, mono- or di-($C_1$–$C_4$-alkyl)aminocarbonyl, cyano, ($C_1$–$C_{12}$-alkyloxy)-carbonyl, phenyl, or phenyl which is monosubstituted or polysubstituted by halogen, in particular fluorine or chlorine.

Particularly preferred agents according to the invention are those with compounds of the formula (I) where X radicals independently of one another are fluorine, chlorine, bromine or trifluoromethyl, preferably in the 2- or 4-position in the phenyl ring, n is 2 or 3, $R^2$ is hydrogen, $C_1$–$C_4$-alkyl, $C_2C_4$-alkenyl or $C_2$–$C_4$-alkynyl, $R^3$ is $C_1$–$C_4$-alkyl which is unsubstituted or monosubstituted or polysubstituted by halogen, or is ($C_1$–$C_{12}$-alkyl)oxycarbonyl or cyano.

Some of the compounds of the formula (I) are known from WO 88/06583 as precursors for the preparation of insecticides and can be prepared in analogy to the processes described therein. The safener action of the compounds of the formula (I) have not been known.

The invention also relates to compounds which have not been previously described, of the mentioned formula (I) in which $R^1$ is cycloalkyl, preferably $C_3$–$C_6$-cycloalkyl, trialkylsilyl, trialkylsilylmethyl or alkyloxyalkyl, preferably ($C_1$–$C_6$-alkoxy)-$C_1$–$C_6$-alkyl, or compounds of the formula (I) in which $(X)_n$ is 2 or 3 radicals on the phenyl ring, preferably two radicals in the 2,3- or 2,4-position, in particular in the 2,4-position, on the phenyl ring, selected from the group comprising halogen and haloalkyl such as, for example, $C_1$–$C_4$-haloalkyl, preferably the radicals 2,4-$Cl_2$, 2,4-$F_2$, 2,4-$Br_2$, 2-Cl-4-F, 2-F-4-Cl, 2,4-$(CF_3)_2$, 2-$CF_3$-4-Cl, 2-Cl-4-$CF_3$, 2-F-4-$CF_3$, 2-$CF_3$-4-F, 2-CF3-4-Br, 2-Br-4-$CF_3$, in particular 2,4-$Cl_2$.

The abovementioned compounds of the formula (I) can be prepared for example by reacting a compound of the formula (II)

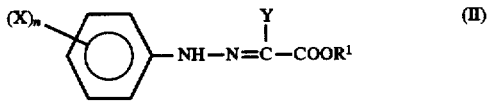

where Y is chlorine or bromine and $(X)_n$ and $R^1$ have the abovementioned meanings, with olefins of the formula III

where $R^2$ and $R^3$ have the abovementioned meanings.

The components can be employed in equimolar amounts or in excess of the compounds of the formula (III), expediently in a molar ratio of from 1:1.05 to 1:20, preferably in a molar ratio of 1:1.1 to 1:5.

Some of the compounds of the formula (II) are known or can be synthesized by customary processes. For example, they can be obtained from the corresponding anilines by diazotization and coupling with the corresponding 2-chloroacetic esters. The compounds of the formula (III) are likewise accessable by customary processes, for example by Witrig olefination of the corresponding ketones or aldehydes of the formula $R^2COR^3$.

The compounds of the formulae (II) and (III) are generally reacted between 0° and 150° C., advantageously between 20° and 100° C., if appropriate in the presence of an organic base, such as sterically hindered amines, for example triethylamine or pyridine, or of an inorganic base such as, for example, potassium carbonate, potassium hydroxide or sodium carbonate, in the presence or absence of an organic solvent such as, if appropriate, a halogenated aliphatic or aromatic hydrocarbon or of an ether, for example of the solvent toluene, xylene, dichloroethane, dimethoxyethane, di- or triglyme, cyclohexane, petroleum ether or chlorobenzene.

The enumeration of bases and solvents is only by way of example, without the process being restricted to these examples.

The compounds of the formula (I) have the property of reducing or completely preventing phytotoxic secondary effects of herbicides when used in crops of useful plants. The compounds of the formula (I) are capable of eliminating harmful secondary effects of the herbicides to a large extent or completely, without impairing the effectiveness of these herbicides against harmful plants. It is possible to considerably enlarge the field of application of conventional herbicides by adding the safener compound of the formula (I).

The present invention therefore also relates to a method of protecting crop plants against pytotoxic secondary effects of herbicides, which comprises treating the plants, seeds of the plants or areas under cultivation with a compound of the formula (I) before, after or simultaneously with, the herbicide.

Examples of herbicides whose phytotoxic secondary effects can be reduced by means of the compounds of the formula (I) are carbamates, thiocarbamates, haloacetanilides, substituted phenoxy-, naphthoxy- and phenoxycarboxylic acid derivatives as well as heteroaryloxyphenoxycarboxylic acid derivatives, such as quinolyloxy-, quinoxalyloxy-, pyridyloxy-, benzoxazolyloxy- and benzothiazolyloxyphenoxycarboxylic esters, and furthermore cyclohexanedione derivatives. Preferred compounds amongst these are phenoxyphenoxy- and heteroaryloxyphenoxycarboxylic esters and structural analogs such as benzylphenoxycarboxylic esters. Suitable esters in this connection are, in particular, lower alkyl, alkenyl and alkynyl esters.

The following herbicides may be mentioned by way of example but without imposing any restriction:

A) Herbicides of the type of the ($C_1$–$C_4$)alkyl, ($C_2$–$C_4$)-alkenyl or ($C_3$–$C_4$)alkynyl phenoxyphenoxy- and heteroaryloxyphenoxycarboxylates, such as methyl 2-(4-(2,4-dichlorophenoxy)phenoxy)propionate,
methyl 2-(4-(4-bromo-2-chlorophenoxy)phenoxy)propionate,
methyl 2-(4-(4-trifluoromethylphenoxy)phenoxy)propionate,
methyl 2-(4-(2-chloro-4-trifluoromethylphenoxy)phenoxy)propionate,
methyl 2-(4-(2,4-dichlorobenzyl)phenoxy)propionate,
2-isopropylideneaminooxyethyl (R)-2-[4-(6chloroquinoxalin-2-yloxy)phenoxy]propionate (propaquizafop),
ethyl 4-(4-(4-trifluoromethylphenoxy)phenoxy)pent-2-enoate,
ethyl 2-(4-(3,5-dichloropyridyl-2-oxy)phenoxy)propionate,
propargyl 2-(4-(3,5-dichloropyridyl-2-oxy)phenoxy) propionate,
ethyl 2-(4-(6-chlorobenzoxazol-2-yloxy)phenoxy) propionate,
ethyl 2-(4-(6-chlorobenzothiazol-2-yloxy)phenoxy) propionate
methyl 2-(4-(3-chloro-5-trifluoromethyl-2-pyridyloxy) phenoxy)propionate,
butyl 2-(4-(5-trifluoromethyl-2-pyridyloxy)phenoxy) propionate,
ethyl 2-(4-(6-chloro-2-quinoxalyloxy)phenoxy)propionate,
ethyl 2-(4-(6-fluoro-2-quinoxalyloxy)phenoxy)propionate,
propargyl 2-(4-(5-chloro-3-fluoropyridyl-2-oxy)phenoxy) propionate
ethyl 2-(4-(b-chloro-2-quinolyloxy)phenoxy)propionate,
trimethylsylylmethyl 2-(4-(3,5-dichloropyridyl-2-oxy) phenoxy)propionate,
ethyl 2-(4-(3-chloro-5-trifluoromethoxy-2-pyridyloxy) phenoxy)propionate, B) Chloroacetanilide herbicides, such as
N-methoxymethyl-2,6-diethylchloroacetanilide,
N-(2-ethyl-6-methylphenyl)-N-(2-methoxy-1-methylethyl)-2-chloroacetamide,
N-(3-methyl-1,2,4-oxadiazol-5-ylmethyl)-2,6-dimethylchloroacetanilide, C) Cyclohexanedione derivatives
S-ethyl-N,N-dipropylthiocarbamate or
S-ethyl-N,N-diisobutylthiocarbamate D) Cyclohexanedione derivatives, such as
2-(N-ethoxybutyrimidoyl)-5-(2-ethylthiopropyl)-3-hydroxy-2-cyclohexen-1-one,
2-(N-ethoxybutyrimidoyl)-5-(2-phenylthiopropyl)-3-hydroxy-2-cyclohexen-1-one,
2-(1-allyloxyiminobutyl)-4-methoxycarbonyl-5,5-dimethyl-3-oxocyclohexenol,
2(N-ethoxypropionamidoyl)-5-mesityl-3-hydroxy-2-cyclohexen-1-one (or also termed 5-(2,4,6-trimethylphenyl)-3-hydroxy-2-[1-(ethoryimino)propyl] cyclohex-2-en-1-one),
2-(N-ethoxybutyrimidoyl)3-hydroxy-5-(thian-3-yl)-2-cyclohexen-1-one.

2-[1(ethoxyimino)butyl]-3-hydroxy-5-(2 H-tetrahydrothiopyran-3-yl)-2-cyclohexen-1-one (BASF 517);

(±)-2-[(E)-3-chloroallyloxyiminopropyl]-5-(2-ethylthiopropyl)-3-hydroxycyclohex-2-enone (clethodim).

Preferred herbicides which may be mentioned from amongst those which can be combined according to the invention with the compounds of the formula (I) are the compounds listed under A), in particular ethyl 2-(4-(6-chlorobenzoxazol-2-yloxy)phenoxy)propionate, ethyl 2-(4-(6-chlorobenzothiazol-2-yloxy)phenoxy)propionate and propargyl 2-(4-(5-chloro-3-fluoropyridyl-2-oxy)phenoxy) propionate. 2-(N-ethoxypropionamidoyl)-5-mesityl-3-hydroxy-2-cyclohexen-1-one is particularly important amongst the substances mentioned under D).

The ratio of safener (compound I): herbicide can vary within wide limits and is preferably between 1:10 and 10:1, in particular 2:1 and 1:10.

The amounts of herbicide and safener which are ideal in each case depend on the type of the herbicide used or on the safener used and also on the nature of the plant stand to be treated, and they can be determined for each individual case by appropriate experiments.

The safeners are mainly employed in particular in cereal crops (wheat, rye, barley, oats), rice, maize and sorghum, but also in cotton, sugar beet, sugar cane and soybean.

Depending on their properties, the safeners can be used for pre-treating the seed of the crop plant, or they can be incorporated in the seed furrows prior to sowing, and used before, after or simultaneously with the herbicide prior to, or after, plant emergence. Pre-emergence treatment includes both the treatment of the cropping area prior to sowing and treatment of the area under cultivation prior to sowing and treatment of the areas under cultivation where seed has been sown but growth of the crop plants has not yet taken place.

However, application of the antidote together with the herbicide is preferred. Tank mixes or ready mixes can be employed for this purpose.

The compounds of the formula (I) or their combinations with one or more of the herbicides or groups of herbicides mentioned can be formulated in a variety of ways, as predetermined by the biological and/or chemical-physical parameters. The following possibilities are therefore suitable for formulation: emulsifiable concentrates (EC), emulsions (EW), suspension concentrates (SC), capsule suspension (sic) (CS), water-soluble concentrates (SL), water-soluble powders (SP), water-soluble granules (SG), water-dispersible powders (sprayable powders) (WP), water-dispersible granules (WG), oil-miscible solutions (OL), dusting agents (DP), granules (GR) in the form of microgranules, spray granules, coated granules and absorption granules, ULV formulations, microcapsules and waxes.

These abovementioned formulation types are known in principle and are described, for example, in: Winnacker-Küchler, "Chemische Technologie [Chemical Technology]", Volume 7, C. Hauser Verlag Munich, 4th Ed., 1986; van Valkenburg, "Pesticides Formulations", Marcel Dekker N.Y., 2nd Ed. 1972-73; K. Martens, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenz-fl achenaktive Äthylenoxiaddukte", Wiss. Verlagsgesellschaft, Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a ready mix or as a tank mix. Wettable powders are preparations which are uniformly dispersible in water and which, besides the active substance, also contain wetting agents, for example polyoxethylated alkylphenols, polyoxethylated fatty alcohols and fatty amines, fatty alcohol polyglycol ether sulfates, alkane- or alkylbenzenesulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of an alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophillite (sic), or diatomaceous earth. Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

In general, the formulations according to the invention contain 1 to 95% by weight, preferably 2 to 90% by weight, of active substance, i.e. active substance of the formula (I) or a combination of the active substance of the formula (I) with the plant protection agent (herbicide).

For example, the concentration of active substance in wettable powders is about 10 to 90% by weight, the remainder to 100% by weight is composed of conventional formulation components. In the case of emulsifiable concentrates, the active substance concentration can be about 1 and (sic) 85% by weight, preferably 5 to 80% by weight. Formulations in the form of dusts usually contain 1 to 25% by weight, preferably 5 to 20% by weight, of active substance, and sprayable solutions about 0.2% to 25% by weight, preferably 2 to 20% by weight, of active substance. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a customary manner, for example with water in the case of wettable powders, emulsifiable concentrates, dispersions and in some instances also in the case of microgranules. Preparations in the form of dusts, soil granules or granules for broadcasting, and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.005 and 10.0 kg/ha or more of active ingredient; preferably, however, it is between 0.01 and 5 kg/ha.

The examples which follow serve to illustrate the invention:

A. Formulation Examples a) A dusting agent is obtained by mixing 10 parts by weight of a compound of the formula (I) and 90 parts by weight of talc or inert substance and comminuting the mixture in a hammer mill.

b) A wettable powder which is readily dispersible in water is obtained by mixing 25 parts by weight of a compound of the formula (I), 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk-mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO=ethylene oxide units) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of oxyethylated nonylphenol as the emulsifier.

e) A concentrate, which is readily emulsifiable in water, of a phenoxycarboxylic acid ester and an antidote (10: 1) is obtained from
12.00% by weight of ethyl 2-[4-(6-chlorobenzoxazol-2-yloxy)phenoxy]propionate,
1.20% by weight of compound of the formula (I)
69.00% by weight of xylene,
7.80% by weight of calcium dodecylbenzenesulfonate,
6.00% by weight of ethoxylated nonylphenol (10 EO) and
4.00% by weight of ethoxylated castor oil (40 EO).
The preparation is carried out as indicated for Example a).

f) A concentrate, which is readily emulsifiable in water, of a phenoxycarboxylic acid ester and an antidote (1:10) is obtained from
4.0% by weight of ethyl 2-[4-(6-chlorobenzoxazol-2-yloxy)phenoxy]propionate,
40.0% by weight of compound of the formula (I),
30.0% by weight of xylene,
20.0% by weight of cyclohexanone,
4.0% by weight of calcium dodecylsulfonate and
2.0% by weight of ethoxylated castor oil (40 EO).

g) Water-dispersible granules are obtained by mixing

| 75 | parts by weight of | a compound of the formula (I), |
| 10 | " | calcium ligninsulfonate, |
| 5 | " | sodium auryl (sic) sulfate, |
| 3 | " | polyvinyl alcohol and |
| 7 | " | kaolin, | grinding the mixture on a pinned disk-mill, and granulating the powder in a fluidized bed by spraying on water as the granulation liquid.

h) Alternatively, water-dispersible granules are obtained by homogenizing and precomminuting, on a colloid mill,

| 25 | parts by weight of | a compound of the formula (I), |
| 5 | " | sodium 2,2'-dinaphthylmethane-6,6'-disulfonate |
| 2 | " | sodium oleolymethyltaurinate (sic), |
| 1 | " | polyvinyl alcohol, |
| 17 | " | calcium carbonate and |
| 50 | " | water, | subsequently grinding the mixture on a bead mill, and atomizing and drying the resulting suspension in a spray tower by means of a single-fluid jet.

i) Granules which are prepared by conventional methods consist of, for example,

| 2–15 | parts by weight of | active substance of the of formula (I), |
| 98–85 | " | inert granulate material, such as attapulgite, pumice and quartz sand. |

EXAMPLE 1

B. Preparation examples

Ethyl 1-(2,4-dichlorophenyl)-5-methyl-5-dodecyloxycarbonylpyrazoline-3-carboxylate 31.8 g of dodecyl methylacrylate and 37.6 g of triethylamine are heated to 70° C. 14.8 g of the 2,4-dichlorophenylhydrazone of ethyl 2-chloroglyoxalate, formula (II)

where $X^1=X^2=Y=Cl$, $R^1=C_2H_5$ (IIa), in 50 ml of toluene, are added dropwise to this mixture in the course of half an hour. Stirring is continued for 4 hours at 80° C., the mixture is allowed to cool, the precipitate is then filtered off with suction, and the filtrate is carefully concentrated in vacuo. Column chromatography (eluent n-heptane/ethyl acetate 1:1) over silica gel gives 19.0 g of the above-described pyrazoline as an oil of refractive index $n_D(20°\,C.):1.5198$.

EXAMPLE 2

Methyl 1-(2,3-dichlorophenyl)-5-cyano-5-methyl-pyrazoline-3-carboxylate 19.0 g of methylacrylonitrile and 7.6 g of triethylamine are heated to 70° C. 14.8 g of the 2,3-dichlorophenylhydrazone of ethyl 2-chloroglyoxalate, (IIb), in 50 ml of dimethoxyethane, are added dropwise to this mixture in the course of half an hour. Stirring is continued for 4 hours at 80° C., the mixture is allowed to cool, the precipitate is filtered off with suction, and the filtrate is carefully concentrated in vacuo. A colorless precipitate (9.2 g) of melting point 66°–67° C. precipitates from the mother liquor.

EXAMPLE 3

Ethyl 1-(2,4-dichlorophenyl)-5-methyl-5-ethoxycarbonylpyrazoline-3-carboxylate 22.8 g of ethyl methylacrylate and 14.8 g of compound of the formula (IIa) (see Example 1) are heated to 50°–60° C. 7.6 g of triethylamine are added dropwise to this mixture in the course of half an hour. Stirring is continued for 2 hours at 70° C., the mixture is allowed to cool, and the precipitate is filtered off with suction, and the filtrate is carefully concentrated under reduced pressure. 18.1 g of pale yellow oil are obtained; refractive index: $n_D(20°\,C.){:}1.5651$.

EXAMPLE 4

Ethyl 1-(2,4-dichlorophenyl)-5-methyl-5-phenylpyrazoline-3-carboxylate 23.7 g of 2-methylstyrene and 14.8 g of compound (IIa) (see Example 1) together with 50 ml saturated aqueous sodium carbonate solution are heated for 4 hours at 80° C. The aqueous phase is subsequently separated off, and the organic phase is dried over sodium sulfate and concentrated under reduced pressure. Column chromatography (eluent n-heptane/ethyl acetate 1:1) over silica gel gives 6.9 g of the above-described pyrazoline as a colorless solid of melting point 87°–89° C.

Table 1 below lists more compounds of the formula (I) which are obtained analogously to the processes of Examples 1 to 4.

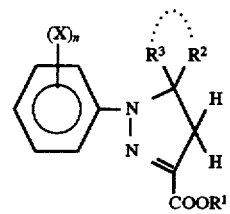

(I)

TABLE 1 pyrazolines of the formula (I)

| Example No. | $(X)_n$ | $R^1$ | $R^2$ | $R^3$ | $n_D^{20}$ [M.p.] |
|---|---|---|---|---|---|
| 5 | 2,4-Cl$_2$ | C$_2$H$_5$ | CH$_3$ | C$_2$H$_5$ | 1.5243 |
| 6 | 2,4-Cl$_2$ | C$_2$H$_5$ | C$_2$H$_5$ | C$_2$H$_5$ | |
| 7 | 2,4-Cl$_2$ | C$_2$H$_5$ | CH$_3$ | n-C$_3$H$_7$ | |
| 8 | 2,4-Cl$_2$ | C$_2$H$_5$ | n-C$_3$H$_7$ | n-C$_3$H$_7$ | |
| 9 | 2,4-Cl$_2$ | C$_2$H$_5$ | CH$_3$ | i-C$_3$H$_7$ | |
| 10 | 2,4-Cl$_2$ | C$_2$H$_5$ | CH$_3$ | t-C$_4$H$_9$ | |
| 11 | 2,4-Cl$_2$ | C$_2$H$_5$ | CH$_3$ | CH$_2$-t-C$_4$H$_9$ | |
| 12 | 2,4-Cl$_2$ | C$_2$H$_5$ | CH$_3$ | CH$_2$Cl | 1.5325 |
| 13 | 2,4-Cl$_2$ | C$_2$H$_5$ | CH$_3$ | CH=CH$_2$ | |
| 14 | 2,4-Cl$_2$ | C$_2$H$_5$ | CH$_3$ | C$_2$H$_4$OH | |
| 15 | 2,4-Cl$_2$ | C$_2$H$_5$ | H | i-C$_3$H$_7$ | |
| 16 | 2,4-Cl$_2$ | C$_2$H$_5$ | H | i-C$_3$H$_5$ | 1.5394 |
| 17 | 2,4-Cl$_2$ | C$_2$H$_5$ | H | CH(OCH$_3$)$_2$ | |
| 18 | 2,4-Cl$_2$ | C$_2$H$_5$ | H | CH(OC$_2$H$_5$)$_2$ | |
| 19 | 2,4-Cl$_2$ | C$_2$H$_5$ | CH$_3$ | C$_2$H$_4$Cl | |
| 20 | 2,4-Cl$_2$ | C$_2$H$_5$ | H | CH$_2$OC$_2$H$_5$ | |
| 21 | 2,4-Cl$_2$ | C$_2$H$_5$ | H | CH$_2$O-n-C$_4$H$_9$ | |
| 22 | 2,4-Cl$_2$ | C$_2$H$_5$ | H | t-C$_4$H$_9$ | |
| 23 | 2,4-Cl$_2$ | C$_2$H$_5$ | H | C$_6$H$_5$ | |
| 24 | 2,4-Cl$_2$ | C$_2$H$_5$ | H | 4-Cl-C$_6$H$_4$ | |
| 25 | 2,4-Cl$_2$ | C$_2$H$_5$ | C$_6$H$_5$ | C$_6$H$_5$ | |
| 26 | 2,4-Br$_2$ | C$_2$H$_5$ | CH$_3$ | C$_6$H$_5$ | |
| 27 | 2-Cl,4-CF$_3$ | C$_2$H$_5$ | CH$_3$ | C$_6$H$_5$ | |
| 28 | 2,4-Cl$_2$ | C$_2$H$_5$ | CH$_3$ | 4-Cl-C$_6$H$_4$ | |
| 29 | 2,4-Cl$_2$ | C$_2$H$_5$ | H | CN | |
| 30 | 2,4-Cl$_2$ | C$_2$H$_5$ | CH$_3$ | CN | |
| 31 | 2,4-Br$_2$ | C$_2$H$_5$ | CH$_3$ | CN | |
| 32 | 2,4-Cl$_2$ | C$_2$H$_5$ | CH$_3$ | Cl | |
| 33 | 2,4-Cl$_2$ | C$_2$H$_5$ | CH$_2$Cl | Cl | |
| 34 | 2,4-Cl$_2$ | C$_2$H$_5$ | C$_2$H$_5$ | Cl | |
| 35 | 2,4-Cl$_2$ | C$_2$H$_5$ | CH$_3$ | CO$_2$CH$_3$ | |
| 36 | 2-CF$_3$,4-Cl | C$_2$H$_5$ | CH$_3$ | CO$_2$C$_2$H$_5$ | |
| 37 | 2,4-Cl$_2$ | C$_2$H$_5$ | CH$_3$ | CO$_2$nC$_4$H$_9$ | |
| 38 | 2,4-Cl$_2$ | C$_2$H$_5$ | CH$_3$ | CO$_2$iC$_4$H$_9$ | 1.5503 |
| 39 | 2,4-Br$_2$ | C$_2$H$_5$ | CH$_3$ | CO$_2$C$_2$H$_5$ | |
| 40 | 2,4-Cl$_2$ | (CH$_2$)$_2$OCH$_3$ | CH$_3$ | CO$_2$CH$_3$ | |
| 41 | 2,3-Cl$_2$ | C$_2$H$_5$ | CH$_3$ | CO$_2$CH$_3$ | |
| 42 | 2-Cl,4-CF$_3$ | C$_2$H$_5$ | CH$_3$ | CO$_2$CH$_3$ | |
| 43 | 2-CF$_3$,4-Cl | C$_2$H$_5$ | CH$_3$ | CO$_2$CH$_3$ | 1.5420 |
| 44 | 2,4-Br$_2$ | C$_2$H$_5$ | CH$_3$ | CO$_2$CH$_3$ | |
| 45 | 2,4-Cl$_2$ | C$_2$H$_5$ | H | CO$_2$CH$_3$ | |
| 46 | 2,4-Cl$_2$ | C$_2$H$_5$ | H | CO$_2$nC$_4$H$_9$ | |
| 47 | 2,4-Cl$_2$ | C$_2$H$_5$ | H | CO$_2$nCl$_{12}$H$_{25}$ | 1.5198 |
| 48 | 2,4-Cl$_2$ | C$_2$H$_5$ | H | CO$_2$CH$_2$Cl | |
| 49 | 2,4-Cl$_2$ | H | H | COOH | [147–150° C.] |
| 50 | 2,4-Cl$_2$ | H | CH$_3$ | CO$_2$H | [178–179° C.] |
| 51 | 2,4-Cl$_2$ | C$_2$H$_5$ | CH$_2$CO$_2$CH$_3$ | CO$_2$CH$_3$ | [82–84° C.] |
| 52 | 2,4-Cl$_2$ | C$_2$H$_5$ | H | COCH$_3$ | |
| 53 | 2,4-Cl$_2$ | C$_2$H$_5$ | CH$_3$ | COCH$_3$ | |

TABLE 1-continued pyrazolines of the formula (I)

| Example No. | $(X)_n$ | $R^1$ | $R^2$ | $R^3$ | $n_D^{20}$ [M.p.] |
|---|---|---|---|---|---|
| 54 | 2,4-$Cl_2$ | $C_2H_5$ | H | $CON(CH_3)_2$ | [149–151° C.] |
| 55 | 2,4-$Cl_2$ | $C_2H_5$ | $CH_3$ | $CON(CH_3)_2$ | [162–163° C.] |
| 56 | 2,4-$Br_2$ | $C_2H_5$ | $CH_3$ | $CO_2$-n-$C_4H_9$ | |
| 57 | 2-$CF_3$,4-Cl | $C_2H_5$ | $CH_3$ | $CO_2C_2H_5$ | |
| 58 | 2-$CF_3$,4-Cl | $C_2H_5$ | $CH_3$ | $C_6H_5$ | |
| 59 | 2,4-$Br_2$ | " | " | $CO_2$-i-$C_4H_9$ | |
| 60 | 2-Cl,4-$CF_3$ | " | " | " | |
| 61 | 2,4-$Br_2$ | " | H | $CH(OC_2H_5)_2$ | |
| 62 | 2,4-$Cl_2$ | " | \multicolumn{2}{c}{—$(CH_2)_4$—} | |
| 63 | " | " | \multicolumn{2}{c}{—$(CH_2)_5$—} | |
| 64 | " | $CH_3$ | H | $CH_3$ | |
| 65 | " | n-$C_6H_{13}$ | $C_2H_5$ | $C_3H_7$ | |
| 66 | " | n-$C_4H_9$ | $C_3H_7$ | F | |
| 67 | " | $CH_3$ | H | cyclo-$C_6H_{11}$ | |
| 68 | " | " | " | cyclobutyl | |
| 69 | " | " | " | cyclopropyl | |
| 70 | " | " | " | cyclopentyl | |
| 71 | " | cyclohexyl | $CH_3$ | $CH_3$ | |
| 72 | " | $CH_2CH_2OCH_2CH_3$ | H | C≡CH | |
| 73 | " | i-$C_3H_7$ | $CH_3$ | $CH_2CH=CH_2$ | |
| 74 | " | $C_2H_5$ | " | $CH_2C≡CH$ | |
| 75 | 2,4-$F_2$ | $CH_3$ | " | CN | |
| 76 | " | $C_2H_5$ | " | $CO_2CH_3$ | |
| 77 | " | $CH_3$ | " | $CF_3$ | |
| 78 | 2,5-$Cl_2$ | $C_2H_5$ | " | $CH_2Cl$ | |
| 79 | " | " | " | $CH_2OH$ | |
| 80 | " | " | " | $CH_2CN$ | |
| 81 | 3,5-$Cl_2$ | " | " | $CH_3$ | |
| 82 | 3,4-$(CF_3)_2$ | $CH_3$ | H | $CF_3$ | |
| 83 | 3,4-$F_2$ | " | " | $CH_2OH$ | |
| 84 | 3-F,4-Cl | " | $C_2H_5$ | $C_2H_5$ | |
| 85 | 3,4-$Cl_2$ | " | " | $CH_2CN$ | |
| 86 | 3-$CF_3$,4-F | " | " | $CO_2CH_3$ | |
| 87 | 2,4,6-$(Cl)_3$ | $C_3H_7$ | H | $CH_3$ | |
| 88 | 2,4,6-$F_3$ | $C_2H_5$ | " | " | |
| 89 | 2-Cl,4-$CF_3$, 6-Cl | $CH_3$ | " | $C_6H_5$ | |
| 90 | 2,4,5-$Cl_3$ | " | $CH_3$ | $CO_2CH_3$ | |
| 91 | 4-Cl | " | " | $CH_3$ | |
| 92 | " | $Si(CH_3)_3$ | " | " | |
| 93 | " | $Si(C_2H_5)_3$ | " | $C_2H_5$ | |
| 94 | 2,4-$Cl_2$ | $Si(CH_3)_3$ | " | " | |
| 95 | " | $CH_2Si(CH_3)_2$ | " | " | |
| 96 | " | " | " | $CO_2CH_3$ | |
| 97 | 2,3-Cl | $Si(CH_3)$ | " | $C_2H_5$ | |
| 98 | " | " | " | $CON(CH_3)_2$ | |
| 99 | " | " | " | 1,1,2,2-$C_2F_4H$ | |
| 100 | 2,4-$Cl_2$ | $Si(C_2H_5)_3$ | " | $CFHCF_2CF_3$ | |
| 101 | 2,4-$Cl_2$ | $C_2H_5$ | H | CO—O$C_2H_5$ | oil |
| 102 | 2,4-$Cl_2$ | $C_2H_5$ | H | CO—O-t-$C_4H_9$ | oil |

EXAMPLE 1

Wheat and barley were grown in plastic pots in the greenhouse until they had reached the 3- to 4-leaf stage and were then treated post-emergence with safener compounds according to the invention and herbicides. The herbicides and the compounds of the formula (I) were applied in these experiments in the form of aqueous suspensions and emulsions at an application rate of 800 l of water/ha (converted). 3 to 4 weeks after treatment, the plants were visually scored for any type of damage by the herbicides applied, with particular regard to the extent of sustained growth inhibition. The degree of damage, or the safener action of compounds of the formula (I) alone or in combination with herbicides, was determined in % damage.

The results show (cf. Table 2) that the compounds according to the invention are capable of effectively reducing extensive herbicide damage on crop plants.

Even when a herbicide such as fenoxaprop-ethyl is used in large overdoses, severe damage which occurs in crop plants is considerably reduced, and lesser damage is entirely eliminated. Mixtures of herbicides and compounds according to the invention are therefore suitable in an advantageous manner for the selective weed control in cereal crops.

TABLE 2 post-emergence safener action

| Compound herbicide + Example No. | Dose (kg of a.i./ha) | % damage in TRAE | % damage in HOVU |
|---|---|---|---|
| H | 2.0 | 70 | — |
|   | 0.2 | — | 80 |
| H + 2 | 2.0 + 1.25 | 30 | — |
|   | 0.2 + 1.25 | — | 50 |
| H + 6 | 2.0 + 1.25 | — | — |

TABLE 2-continued post-emergence safener action

| Compound herbicide + Example No. | Dose (kg of a.i./ha) | % damage in TRAE | % damage in HOVU |
|---|---|---|---|
| H + 7 | 0.2 + 1.25 | — | 20 |
|  | 2.0 + 1.25 | — | — |
| H + 8 | 0.2 + 1.25 | — | 30 |
|  | 2.0 + 1.25 | — | — |
| H + 13 | 0.2 + 1.25 | — | 35 |
|  | 2.0 + 1.25 | 20 | — |
| H + 16 | 0.2 + 1.25 | — | 30 |
|  | 2.0 + 1.25 | 10 | — |
| H + 17 | 0.2 + 1.25 | — | 10 |
|  | 2.0 + 1.25 | — | — |
| H + 25 | 0.2 + 1.25 | — | 35 |
|  | 2.0 + 1.25 | — | — |
| H + 29 | 0.2 + 1.25 | — | 20 |
|  | 2.0 + 1.25 | 40 | — |
| H + 30 | 0.2 + 1.25 | — | 40 |
|  | 2.0 + 1.25 | 40 | — |
| H + 45 | 0.2 + 1.25 | — | 30 |
|  | 2.0 + 1.25 | 20 | — |
| H + 47 | 0.2 + 1.25 | — | 27 |
|  | 2.0 + 1.25 | — | — |
| H + 49 | 0.2 + 1.25 | — | 27 |
|  | 2.0 + 1.25 | 20 | — |
| H + 52 | 0.2 + 1.25 | — | 45 |
|  | 2.0 + 1.25 | — | — |
| H + 62 | 0.2 + 1.25 | — | 17 |
|  | 2.0 + 1.25 | — | — |
|  | 0.2 + 1.25 | — | 30 |

Abbreviations:
Example No.=number of the preparation example from Part B (see Examples 1 to 4 and Table 1)
H=fenoxaprop-ethyl
TRAE=Triticum aestivum (Wheat)
HOVU=Hordeumvulgare (Barley)
a.i.=active ingredient; based on pure active substance

EXAMPLE 2

A trial series analogous to Example 1, but with a larger number of replicate trials for each application, gave the results shown in Table 3. Some of the absolute values differ in their effectiveness, which can be attributed to climatic effects which were not entirely identical in the two trial series.

TABLE 3

Safener action of the compounds according to the invention on wheat (TRAE) and barley (HOVU).

| Herbicide + safener (Example No.) | Dose (kg of a.i./ha) | Herbicidal action in % TRAE | Herbicidal action in % HOVU |
|---|---|---|---|
| H | 2.0 | 70 | — |
|  | 0.2 | — | 85 |
| H + 1 | 2.0 + 1.0 | 20 | — |
|  | 2.0 + 0.25 | 8 | — |
|  | 0.2 + 1.0 | — | 40 |
|  | 0.2 + 0.25 | — | 42 |
| H + 2 | 2.0 + 1.0 | 30 | — |
|  | 2.0 + 0.25 | 20 | — |
|  | 0.2 + 1.0 | — | 15 |
|  | 0.2 + 0.25 | — | 25 |
| H + 3 | 2.0 + 1.0 | 18 | — |
|  | 2.0 + 0.25 | 10 | — |
|  | 0.2 + 1.0 | — | 15 |
|  | 0.2 + 0.25 | — | 18 |
| H + 6 | 2.0 + 1.0 | 5 | — |
|  | 2.0 + 0.25 | 10 | — |
|  | 0.2 + 1.0 | — | 12 |
|  | 0.2 + 0.25 | — | 15 |
| H + 7 | 2.0 + 1.0 | 20 | — |
|  | 2.0 + 0.25 | 22 | — |
|  | 0.2 + 1.0 | — | 20 |
|  | 0.2 + 0.25 | — | 22 |
| H + 8 | 2.0 + 1.0 | 20 | — |
|  | 2.0 + 0.25 | 25 | — |
|  | 0.2 + 1.0 | — | 25 |
|  | 0.2 + 0.25 | — | 27 |
| H + 11 | 2.0 + 1.0 | 48 | — |
|  | 2.0 + 0.25 | 50 | — |
|  | 0.2 + 1.0 | — | 32 |
|  | 0.2 + 0.25 | — | 40 |
| H + 13 | 2.0 + 1.0 | 10 | — |
|  | 2.0 + 0.25 | 12 | — |
|  | 0.2 + 1.0 | — | 35 |
|  | 0.2 + 0.25 | — | 35 |
| H + 15 | 2.0 + 1.0 | 2 | — |
|  | 2.0 + 0.25 | 5 | — |
|  | 0.2 + 1.0 | — | 32 |
|  | 0.2 + 0.25 | — | 40 |
| H + 16 | 2.0 + 1.0 | 10 | — |
|  | 2.0 + 0.25 | 12 | — |
|  | 0.2 + 1.0 | — | 28 |
|  | 0.2 + 0.25 | — | 37 |
| H + 17 | 2.0 + 1.0 | 22 | — |
|  | 2.0 + 0.25 | 25 | — |
|  | 0.2 + 1.0 | — | 30 |
|  | 0.2 + 0.25 | — | 35 |
| H + 18 | 2.0 + 1.0 | 20 | — |
|  | 2.0 + 0.25 | 13 | — |
|  | 0.2 + 1.0 | — | 30 |
|  | 0.2 + 0.25 | — | 27 |
| H + 20 | 2.0 + 1.0 | 15 | — |
|  | 2.0 + 0.25 | 10 | — |
|  | 0.2 + 1.0 | — | 38 |
|  | 0.2 + 0.25 | — | 45 |
| H + 21 | 2.0 + 1.0 | 20 | — |
|  | 2.0 + 0.25 | 25 | — |
|  | 0.2 + 1.0 | — | 30 |
|  | 0.2 + 0.25 | — | 35 |
| H + 25 | 2.0 + 1.0 | 10 | — |
|  | 2.0 + 0.25 | 12 | — |
|  | 0.2 + 1.0 | — | 10 |
|  | 0.2 + 0.25 | — | 15 |
| H + 29 | 2.0 + 1.0 | — | — |
|  | 2.0 + 0.25 | — | — |
|  | 0.2 + 1.0 | — | 30 |
|  | 0.2 + 0.25 | — | 40 |
| H + 30 | 2.0 + 1.0 | 30 | — |
|  | 2.0 + 0.25 | 20 | — |
|  | 0.2 + 1.0 | — | 12 |
|  | 0.2 + 0.25 | — | 25 |
| H + 31 | 2.0 + 1.0 | 10 | — |
|  | 2.0 + 0.25 | 15 | — |
|  | 0.2 + 1.0 | — | 30 |
|  | 0.2 + 0.25 | — | 38 |
| H + 35 | 2.0 + 1.0 | 22 | — |
|  | 2.0 + 0.25 | 25 | — |
|  | 0.2 + 1.0 | — | 20 |
|  | 0.2 + 0.25 | — | 35 |
| H + 36 | 2.0 + 1.0 | 18 | — |
|  | 2.0 + 0.25 | 25 | — |
|  | 0.2 + 1.0 | — | 20 |
|  | 0.2 + 0.25 | — | 35 |
| H + 37 | 2.0 + 1.0 | 35 | — |
|  | 2.0 + 0.25 | 38 | — |
|  | 0.2 + 1.0 | — | 20 |

TABLE 3-continued

Safener action of the compounds according to the invention on wheat (TRAE) and barley (HOVU).

| Herbicide + safener (Example No.) | Dose (kg of a.i./ha) | Herbicidal action in % TRAE | HOVU |
|---|---|---|---|
|  | 0.2 + 0.25 | — | 28 |
| H + 38 | 2.0 + 1.0 | 5 | — |
|  | 2.0 + 0.25 | 8 | — |
|  | 0.2 + 1.0 | — | 35 |
|  | 0.2 + 0.25 | — | 38 |
| H + 39 | 2.0 + 1.0 | 15 | — |
|  | 2.0 + 0.25 | 23 | — |
|  | 0.2 + 1.0 | — | 30 |
|  | 0.2 + 0.25 | — | 23 |
| H + 40 | 2.0 + 1.0 | 18 | — |
|  | 2.0 + 0.25 | 23 | — |
|  | 0.2 + 1.0 | — | 10 |
|  | 0.2 + 0.25 | — | 13 |
| H + 43 | 2.0 + 1.0 | 23 | — |
|  | 2.0 + 0.25 | 10 | — |
|  | 0.2 + 1.0 | — | 20 |
|  | 0.2 + 0.25 | — | 35 |
| H + 44 | 2.0 + 1.0 | 15 | — |
|  | 2.0 + 0.25 | 13 | — |
|  | 0.2 + 1.0 | — | 25 |
|  | 0.2 + 0.25 | — | 25 |
| H + 45 | 2.0 + 1.0 | 5 | — |
|  | 2.0 + 0.25 | 10 | — |
|  | 0.2 + 1.0 | — | 15 |
|  | 0.2 + 0.25 | — | 25 |
| H + 47 | 2.0 + 1.0 | 3 | — |
|  | 2.0 + 0.25 | 5 | — |
|  | 0.2 + 1.0 | — | 38 |
|  | 0.2 + 0.25 | — | 40 |
| H + 48 | 2.0 + 1.0 | 28 | — |
|  | 2.0 + 0.25 | 10 | — |
|  | 0.2 + 1.0 | — | 30 |
|  | 0.2 + 0.25 | — | 40 |
| H + 49 | 2.0 + 1.0 | 10 | — |
|  | 2.0 + 0.25 | 20 | — |
|  | 0.2 + 1.0 | — | 45 |
|  | 0.2 + 0.25 | — | 50 |
| H + 50 | 2.0 + 1.0 | 20 | — |
|  | 2.0 + 0.25 | 25 | — |
|  | 0.2 + 1.0 | — | 35 |
|  | 0.2 + 0.25 | — | 37 |
| H + 51 | 2.0 + 1.0 | 25 | — |
|  | 2.0 + 0.25 | 23 | — |
|  | 0.2 + 1.0 | — | 33 |
|  | 0.2 + 0.25 | — | 48 |
| H + 52 | 2.0 + 1.0 | 22 | — |
|  | 2.0 + 0.25 | 28 | — |
|  | 0.2 + 1.0 | — | 25 |
|  | 0.2 + 0.25 | — | 30 |
| H + 56 | 2.0 + 1.0 | 10 | — |
|  | 2.0 + 0.25 | 28 | — |
|  | 0.2 + 1.0 | — | 30 |
|  | 0.2 + 0.25 | — | 30 |
| H + 57 | 2.0 + 1.0 | 13 | — |
|  | 2.0 + 0.25 | 10 | — |
|  | 0.2 + 1.0 | — | 20 |
|  | 0.2 + 0.25 | — | 18 |
| H + 60 | 2.0 + 1.0 | 10 | — |
|  | 2.0 + 0.25 | 8 | — |
|  | 0.2 + 1.0 | — | 48 |
|  | 0.2 + 0.25 | — | 50 |
| H + 61 | 2.0 + 1.0 | 0 | — |
|  | 2.0 + 0.25 | 0 | — |
|  | 0.2 + 1.0 | — | 20 |
|  | 0.2 + 0.25 | — | 25 |
| H + 62 | 2.0 + 1.0 | 22 | — |
|  | 2.0 + 0.25 | 25 | — |
|  | 0.2 + 1.0 | — | 35 |
|  | 0.2 + 0.25 | — | 40 |
| H + 101 | 2.0 + 1.0 | 10 | — |
|  | 2.0 + 0.25 | 12 | — |
|  | 0.2 + 1.0 | — | 12 |
|  | 0.2 + 0.25 | — | 20 |
| H + 102 | 2.0 + 1.0 | 25 | — |
|  | 2.0 + 0.25 | 30 | — |
|  | 0.2 + 1.0 | — | 20 |
|  | 0.2 + 0.25 | — | 28 |

Abbreviations:
Example No.=number of the preparation example from Part B (see Examples 1 to 4 and Table 1)
H=fenoxaprop-ethyl
TRAE=Triticum aestivum (Wheat)
HOVU=Hordeumvulgare (Barley)
a.i.=active ingredient; based on pure active substance

We claim:

1. A method for protecting crop plants against phytotoxic effects of herbicides wherein a compound of formula (I)

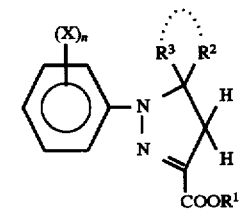

where
X radicals independently of one another are halogen or haloalkyl,
n is an integer from 1 to 3,
$R^1$ is hydrogen, alkyl, cycloalkyl, trialkylsilyl, trialkylsilylmethyl or alkyloxyalkyl,
$R^2$ and $R^3$ independently of one another are hydrogen, alkyl, $C_3$–$C_6$-cycloalkyl, alkenyl, alkynyl, haloalkyl, alkoxyalkyl, hydroxyalkyl, alkoxycarbonyl, alkylcarbonyl, alkylaminocarbonyl, optionally substituted phenyl, halogen or cyano, it being possible for the radicals $R^2$ and $R^3$ to form a ring with the 5-C atom of the pyrazoline ring, is used as a safener.

2. A method as claimed in claim 1, wherein
X radicals independently of one another are halogen or $C_1$–$C_4$-haloalkyl,
n is an integer from 1 to 3,
$R^1$ is $C_1$–$C_6$-alkyl, $C_3$–$C_6$-cycloalkyl, tri($C_1$–$C_4$-alkyl)silyl, tri($C_1$–$C_4$-alkyl)silylmethyl or ($C_1$–$C_6$-alkyl-oxy)-$C_1$–$C_6$-alkyl,
$R^2$ and $R^3$ independently of one another are halogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, mono- or di-($C_1$–$C_4$-alkoxy)-$C_1$–$C_4$-alkyl, $C_1$–$C_6$-hydroxyalkyl, ($C_1$–$C_6$-alkyl)carbonyl, mono- or di-($C_1$–$C_4$-alkyl)aminocarbonyl, cyano, halogen, ($C_1$–$C_{12}$-alkyl)oxycarbonyl, phenyl, or phenyl which is substituted by one or more radicals selected from the group comprising halogen, $C_1$–$C_4$-alkyl, $C_1$–$C_4$-alkoxy or cyano.

3. A method as claimed in claim 1, wherein
X radicals independently of one another are fluorine, chlorine, bromine or trifluoromethyl,
n is 2 or 3,
$R^1$ is $C_1$–$C_4$-alkyl or ($C_1$–$C_4$-alkoxy)-$C_1$–$C_4$-alkyl, $R^2$ is hydrogen, $C_1$–$C_4$-alkyl or $C_2$–$C_4$-alkenyl, $R^3$ is $C_1$–$C_4$-alkyl, $C_3$–$C_4$-alkenyl, $C_2$–$C_4$-alkynyl, $C_1$–$C_4$-haloalkyl, mono- or di-($C_1$–$C_4$-alkoxy)-$C_1$–$C_4$-alkyl, $C_1$–$C_4$-hydroxyalkyl, mono- or di-($C_1$–$C_4$-alkyl)-amino-carbonyl, cyano, ($C_1$–$C_{12}$-alkyloxy)carbonyl, phenyl, or phenyl which is monosubstituted or polysubstituted by halogen.

4. A method as claimed in 1, wherein

X radicals independently of one another are fluorine, chlorine, bromine or trifluoromethyl, n is 2 or 3, $R^2$ is hydrogen, $C_1$–$C_4$-alkyl, $C_2$–$C_4$-alkenyl or $C_2$–$C_4$-alkynyl, and $R^3$ is $C_1$–$C_4$-alkyl which is unsubstituted or monosubstituted or polysubstituted by halogen, or is ($C_1$–$C_{12}$-alkyl)oxycarbonyl or cyano.

5. A method as claimed in claim 1, wherein

X radicals independent of one another are halogen or haloalkyl n is 1, 2 or 3, $R^1$ is H or $C_1$–$C_4$-alkyl, $R^2$ is H or $C_1$–$C_4$-alkyl, $R^3$ is $C_1$–$C_4$-alkyl or ($C_1$–$C_{12}$-alkoxy)-carbonyl.

6. A method as claimed in claim 5, wherein $(X)_n$ is 2,4-dichloro, $R^1$ is $C_1$–$C_4$-alkyl, $R^2$ is hydrogen or methyl, $R^3$ is ($C_1$–$C_4$-alkoxy)-carbonyl.

7. A method as claimed in claim 1, wherein the molar ratio of safener and herbicide is between 1:10 and 10:1.

8. A method as claimed in claim 1, wherein the herbicide is selected from the group consisting of carbamates, thiocarbamates, haloacetanilides, substituted phenoxycarboxylic acid derivatives, substituted naphthoxycarboxylic acid derivatives, substituted phenoxyphenoxycarboxylic acid derivatives, heteroaryloxyphenoxycarboxylic acid derivatives and cyclohexandione derivatives.

9. A method as claimed in claim 8, wherein the herbicide is selected from the group consisting of substituted phenoxyphenoxycarboxylic acid derivatives and heteroaryloxyphenoxycarboxylic acid derivatives.

10. A method as claimed in claim 9, wherein the herbicide is fenoxaprop-ethyl or fenoxaprop-P-ethyl.

11. A method as claimed in claim 1, which comprises applying the herbicide in combination with the safener compound of formula (I), to the plants, seeds of the plants or the area under cultivation.

12. A method as claimed in claim 1, wherein a formulation containing the herbicide and the safener together with common formulation auxiliaries is used.

13. A method as claimed in claim 1, wherein each of the herbicide and the safener are separately formulated with common formulation auxiliaries and the separate formulations are used together.

14. A method for protecting crop plants against phytotoxic effects of herbicides, wherein the herbicide is fenoxaprop-ethyl or fenoxaprop-P-ethyl, wherein a compound of formula (I)

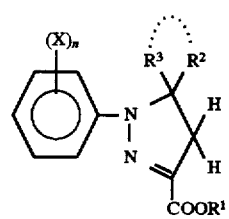

where

X radicals independently of one another are halogen or haloalkyl, n is an integer from 1 to 3, $R^1$ is hydrogen, alkyl, cycloalkyl, trialkylsilyl, trialkylsilylmethyl or alkyloxyalkyl, $R^2$ and $R^3$ independently of one another are hydrogen, alkyl, $C_3$–$C_6$-cycloalkyl, alkenyl, alkynyl, haloalkyl, alkoxyalkyl, hydroxyalkyl, alkoxycarbonyl, alkylcarbonyl, alkylaminocarbonyl, optionally substituted phenyl, halogen or cyano, it being possible for the radicals $R^2$ and $R^3$ to form a ring with the 5-C atom of the pyrazoline ring, is used as a safener.

15. A method for protecting crop plants against phytotoxic effects of herbicides, wherein the herbicide is fenoxaprop-ethyl or fenoxaprop-P-ethyl wherein a compound of formula (I)

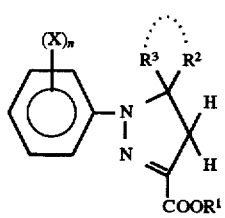

where

X radicals independently of one another are halogen or haloalkyl, n is an integer from 1 to 3, $R^1$ is hydrogen, alkyl, cycloalkyl, trialkylsilyl, trialkylsilylmethyl or alkyloxyalkyl, $R^2$ and $R^3$ independently of one another are hydrogen, alkyl, $C_3$–$C_6$-cycloalkyl, alkenyl, alkynyl, haloalkyl, alkoxyalkyl, hydroxyalkyl, alkoxycarbonyl, alkyl, carbonyl, alkylaminocarbonyl, optionally substituted phenyl, halogen or cyano, it being possible for the radicals $R^2$ and $R^3$ to form a ring with the 5-C atom of the pyrazoline ring, is used as a safener, and wherein the molar ratio of safener and herbicide is between 1:10 and 10:1, and wherein the herbicide in combination with the safener compound is applied to the plants, seeds of the plants or the area under cultivation.

16. A method for protecting crop plants against phytotoxic side effects of a herbicide selected from the group consisting of fenoxaprop-ethyl and fenoxaprop-P-ethyl, wherein a compound of formula (I)

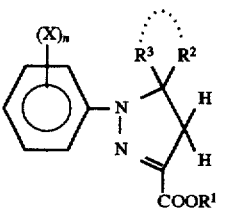

where

X radicals independently of one another are halogen or haloalkyl, n is an integer from 1 to 3, $R^1$ is hydrogen, alkyl, cycloalkyl, trialkylsilyl, trialkylsilylmethyl or alkyloxyalkyl, $R^2$ and $R^3$ independently of one another are hydrogen, alkyl, $C_3$–$C_6$-cycloalkyl, alkenyl, alkynyl, haloalkyl, alkoxyalkyl, hydroxyalkyl, alkoxycarbonyl, alkylcarbonyl, alkylaminocarbonyl, optionally substituted phenyl, halogen or cyano, it being possible for the radicals $R^2$ and $R^3$ to form a ring with the 5-C atom of the pyrazoline ring, is used as a safener.

17. A method as claimed in claim 16, which comprises applying the herbicide in combination with the safener compound of formula (I) to the plants, seeds of the plants or the area under cultivation.

18. A method as claimed in claim 17, wherein

X radicals independently of one another are halogen or $C_1$–$C_4$-haloalkyl, n is an integer from 1 to 3, $R^1$ is $C_1$–$C_6$-alkyl, $C_3$–$C_6$-cycloalkyl, tri($C_1$–$C_4$-alkyl)silyl, tri ($C_1$–$C_4$-alkyl) silylmethyl or ($C_1$–$C_6$-alkyloxy)-$C_1$–$C_6$-alkyl, $R^2$ and $R^3$ independently of one another are halogen, $C_{1-C6}$-alkyl, $C_2$–$C_6$-alkenyl, $C_2$–$C_6$-alkynyl, $C_3$–$C_6$-cycloalkyl, $C_1$–$C_6$-haloalkyl, mono- or di-($C_1$–$C_4$-alkoxy)-$C_1$–$C_4$-alkyl, $C_1$–$C_6$-hydroxyalkyl, ($C_1$–$C_6$-alkyl) carbonyl, mono- or di- ($C_1$–$C_4$-alkyl) aminocarbonyl, cyano, halogen, ($C_1$–$C_{12}$-alkyl)oxycarbonyl, phenyl, or phenyl which is substituted by one or more radicals selected from the group comprising halogen, $C_1$–$C_4$-alkyl, $C_1$–$C_4$-alkoxy or cyano.

19. A method as claimed in claim 17, wherein

X radicals independently of one another are fluorine, chlorine, bromine or trifluoromethyl, n is 2 or 3, $R^1$ is $C_1$–$C_4$-alkyl or ($C_1$–$C_4$-alkoxy)-$C_1$–$C_4$-alkyl, $R^2$ is hydrogen, $C_1$–$C_4$-alkyl or $C_2$–$C_4$-alkenyl, $R^3$ is $C_1$–$C_4$-alkyl, $C_3$–$C_4$-alkenyl, $C_2$–$C_4$-alkynyl, $C_1$–$C_4$-haloalkyl, mono- or di- ($C_1$–$C_4$-alkoxy) -$C_1$–$C_4$-alkyl, $C_1$–$C_4$-hydroxyalkyl, mono- or di-($C_1$–$C_4$-alkyl)-amino-carbonyl, cyano, ($C_1$–$C_{12}$-alkyloxy)carbonyl, phenyl, or phenyl which is monosubstituted or polysubstituted by halogen.

20. A method as claimed in claim 17 wherein

X radicals independently of one another are fluorine, chlorine, bromine or trifluoromethyl, n is 2 or 3, $R^2$ is hydrogen, $C_1$–$C_4$-alkyl, $C_2$–$C_4$-alkenyl or $C_2$–$C_4$-alkynyl, and $R^3$ is $C_1$–$C_4$-alkyl which is unsubstituted or monosubstituted or polysubstituted by halogen, or is ($C_1$–$C_{12}$-alkyl)oxycarbonyl or cyano.

21. A method as claimed in claim 17, wherein:

X radicals independent of one another are halogen or haloalkyl n is 1, 2 or 3, $R^1$ is H or $C_1$–$C_4$-alkyl, $R^2$ is H or $C_1$–$C_4$-alkyl, $R^3$ is $C_1$–$C_4$-alkyl or ($C_1$–$C_{12}$-alkoxy)-carbonyl.

22. A method as claimed in claim 21, wherein $(X)_n$ is 2,4-dichloro, $R^1$ is $C_1$–$C_4$-alkyl, $R^2$ is hydrogen or methyl, $R^3$ is ($C_1$–$C_4$-alkoxy)-carbonyl.

23. A method as claimed in claim 22, wherein $R^2$ is methyl.

24. A compound of the formula (I)

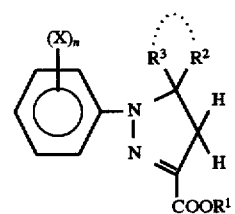

(I)

where

X radicals independently of one another are halogen or haloalkyl, n is 1, 2 or 3, $R^1$ is cycloalkyl, trialkylsilyl, trimethylsilylmethyl or alkoxyalkyl, $R^2$ and $R^3$ independently of one another are hydrogen, alkyl, $C_3$–$C_6$-cycloalkyl, alkenyl, alkynyl, haloalkyl, alkoxyalkyl, hydroxyalkyl, alkoxycarbonyl, alkylcarbonyl, alkylaminocarbonyl, optionally substituted phenyl, halogen or cyano, it being possible for the radicals $R^2$ and $R^3$ to form a ring with the 5-C atom of the pyrazoline ring.

25. A compound as claimed in claim 24, wherein the

X radicals independently of one another are halogen or $C_1$–$C_4$-haloalkyl, n is 1, 2 or 3, $R^1$ is $C_3$–$C_6$-cycloalkyl, tri ($C_1$–$C_4$-alkyl)silyl, trimethylsilylmethyl or $C_1$–$C_6$-alkoxy-$C_1$–$C_6$-alkyl, $R^2$ and $R^3$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, mono- or di- ($C_1$–$C_4$-alkoxy)-$C_1$–$C_4$-alkyl, $C_{1-C6}$-hydroxyalkyl, ($C_1$–$C_6$-alkyl) carbonyl, mono- or di-($C_1$–$C_4$-alkyl) aminocarbonyl, cyano, halogen, ($C_1$–$C_{12}$-alkyl) oxycarbonyl, phenyl, or phenyl which is substituted by one or more radicals selected from the group comprising halogen, $C_1$–$C_4$-alkyl, $C_1$–$C_4$-alkoxy or cyano.

26. A compound as claimed in claim 25, wherein $(X)_n$ is two radicals selected from the group comprising halogen and $C_1$–$C_4$-haloalkyl.

27. A compound as claimed in claim 25, wherein $(X)_n$ is 2,4-$C_2$, 2,4-$F_2$, 2,4-$Br_2$, 2-Cl-4-F, 2-F-4-Cl, 2,4-$(CF_3)_2$, 2-$CF_3$-4-Cl, 2-Cl-4-$CF_3$, 2-F-4-$CF_3$, 2-$CF_3$-4-F, 2-$CF_3$-4-Br or 2-Br-4-$CF_3$.

28. A compound of the formula (I)

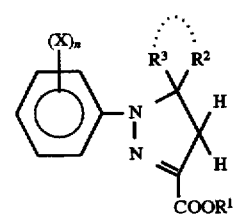

(I)

wherein (X) n is 2,4-dichloro, $R^1$ is ethyl, $R^2$ is methyl and $R^3$ is ethoxycarbonyl.

29. A compound of the formula (I),
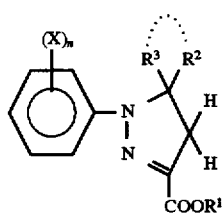
where
$(X)_n$ is 2,4-dichloro,
$R^1$ is $C_1$–$C_6$-alkyl,
$R^2$ is $C_1$–$C_4$-aklyl,
$R^3$ is ($C_1$–$C_{12}$-alkoxy)-carbonyl.
30. A compound as claimed in claim 29, where
$R^1$ is $C_1$–$C_4$-aklyl, and
$R^3$ is ($C_1$–$C_{12}$-alkoxy)-carbonyl.
31. A compound as claimed in claim 30, wherein $R^2$ is methyl.
* * * * *